(12) United States Patent
Struempler et al.

(10) Patent No.: US 7,324,910 B2
(45) Date of Patent: Jan. 29, 2008

(54) SENSOR ARRAY FOR NAVIGATION ON SURFACES

(75) Inventors: Ralf Struempler, Erding (DE); Wolf-Dietrich Kleinert, Bonn (DE)

(73) Assignee: General Electric Company, Niskayuna, NY (US)

( * ) Notice: Subject to any disclaimer, the term of this patent is extended or adjusted under 35 U.S.C. 154(b) by 15 days.

(21) Appl. No.: 11/317,098

(22) Filed: Dec. 22, 2005

(65) Prior Publication Data

US 2007/0150238 A1 Jun. 28, 2007

(51) Int. Cl.
*G01C 25/00* (2006.01)
*G06F 15/00* (2006.01)

(52) U.S. Cl. ..................... 702/116; 702/189
(58) Field of Classification Search .............. 702/38, 702/39, 116, 168; 324/533, 534, 750–751; 250/370.01, 370.08, 208.1; 600/437, 475, 600/476
See application file for complete search history.

(56) References Cited

U.S. PATENT DOCUMENTS 6,494,836 B2 * 12/2002 Ogawa ................. 600/443
6,641,535 B2   11/2003 Buschke et al.
6,790,182 B2 *  9/2004 Eck et al. ................ 600/447
6,816,743 B2 * 11/2004 Moreno et al. ........... 600/473

FOREIGN PATENT DOCUMENTS

WO     WO 02/42762 A1    5/2002

* cited by examiner

*Primary Examiner*—Bryan Bui
(74) *Attorney, Agent, or Firm*—Richard A. DeCristofaro; Patrick K. Patnode

(57) ABSTRACT

A probe system is provided that includes a linear and/or two-dimensional sensor array for obtaining information regarding a test piece. The sensor elements of the sensor array may include ultrasonic, eddy current, magnetic, and/or piezoelectric elements. The sensor array may be utilized to detect movement of the probe with respect to the test piece, and may be further utilized to obtain data regarding the test piece, such as image data, for example with respect to a characteristic of the test piece in detecting and locating flaws. A CAD type file or other graphical or image file of the test piece may be displayed concurrently with image data of the test piece obtained by the probe for example to assist an operator in navigating the probe with respect to the test piece, and/or to determine a coordinate location of characteristics of the test piece with respect to the CAD type file.

26 Claims, 5 Drawing Sheets

SENSOR ARRAY FOR NAVIGATION ON SURFACES

BACKGROUND

Portable ultrasonic detectors are frequently used in inspection applications. Typical objects of inspection may include welded steel parts for example steel tubes. The ultrasonic detector may be coupled by a grease, an oil or water to the part, and the inspector may move the detector in various zigzag type movements to areas of interests such as a weld or a corroded backwall, or away from it to other areas. Using such an instrument, flaws in the part or bad welds may be observed. As the movement of the detector-is random and undetermined, it is often difficult to image the detected failures in relation to the dimensions and design features of the part and the probe position. As the parts may be complex, for example tubes, T-joints, and so on, the geometry of the parts may increase the difficulty of inspecting such parts and identifying the coordinates of any detected flaws in dependence of the probe position.

SUMMARY

In accordance with one aspect of the system described herein, an apparatus having a transmitter and an array of sensors is provided. The transmitter transmits a signal capable of at least partially penetrating a test piece. The array includes one or more sensors capable of detecting at least a portion of the signal reflected back from the test piece. In addition, the apparatus includes an information handling system configured to receive data from the array. The information handling system determines at least one of: movement data of the array; data of a characteristic of the test piece; and a combination of the two.

In accordance with an aspect of the techniques described herein, a method having the steps of transmitting a signal, detecting a portion of the reflected signal, and determining data is shown. A signal capable of at least partially penetrating a test piece is transmitted. At least a portion of the signal reflected from the test piece is detected, and in response to detecting the portion of the reflected signal, at least one of movement data or data of a characteristic of the test piece is determined. Image data of the test piece is generated based on the movement data or characteristics determined. The image data is displayed concurrently with an image of the test piece based on a data file.

In accordance with another aspect of the systems described herein, a probe system having an information handling system and a probe is described. The probe is capable of coupling with the information handling system. The probe includes a transmitter and an array as described above.

In accordance with yet another aspect of the system described herein, the sensor array may be formed using a grid of sensors arranged in a first number of rows and a second number of columns.

DESCRIPTION OF THE DRAWING FIGURES

Claimed subject matter is particularly pointed out and distinctly claimed in the concluding portion of the specification. However, both as to organization and/or method of operation, together with objects, features, and/or advantages thereof, may best be understood by reference to the following detailed description when read with the accompanying drawings in which:

Figure 1:
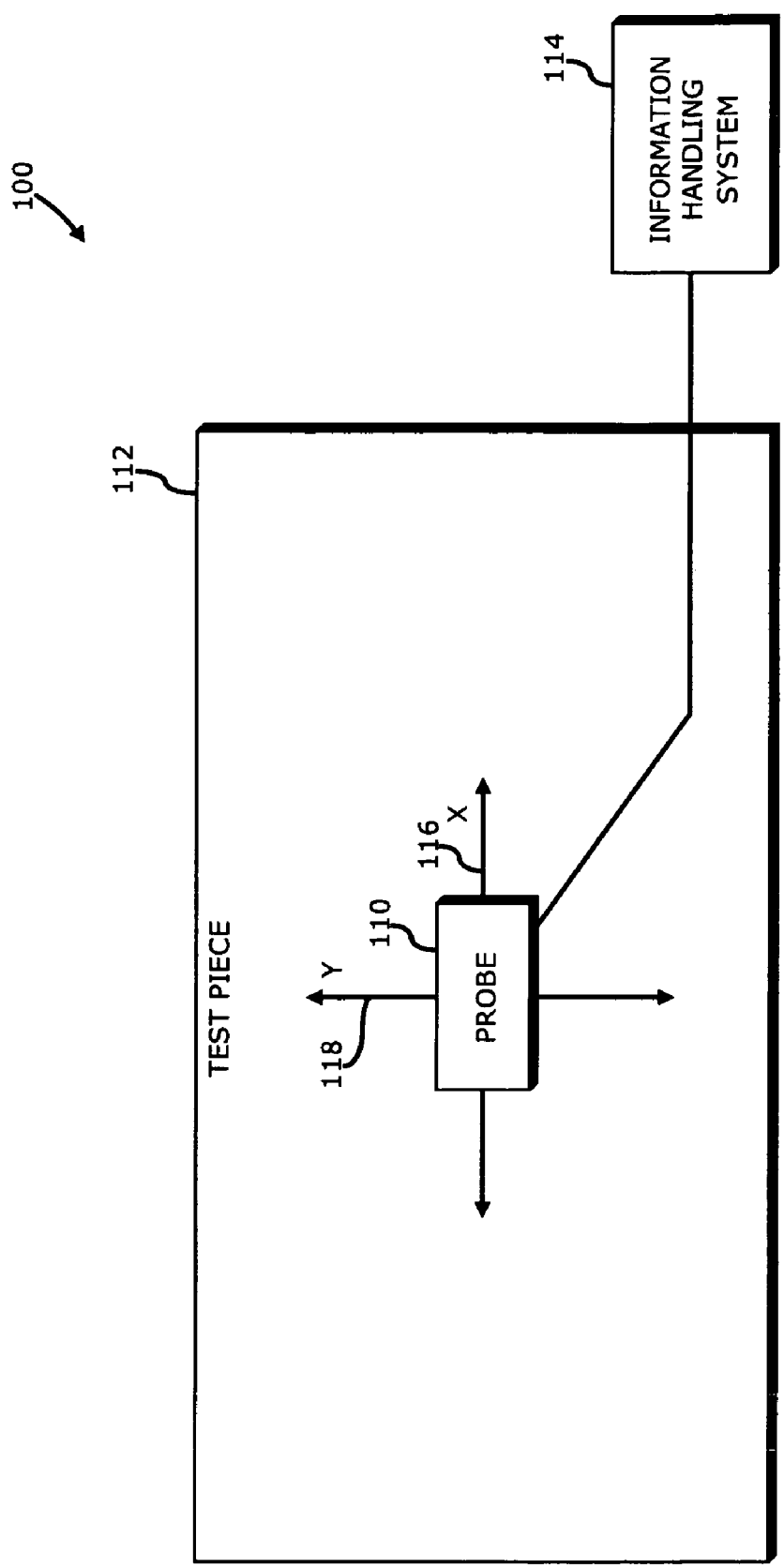
FIG. 1 is a block diagram of a probe system in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding or analogous elements.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail.

Some portions of the detailed description that follows are presented in terms of algorithms, programs and/or symbolic representations of operations on data bits or binary digital signals within a computer memory, for example. These algorithmic descriptions and/or representations may include techniques used in the data processing arts to convey the arrangement of a computer system and/or other information handling system to operate according to such programs, algorithms, and/or symbolic representations of operations.

A program and/or process may be generally considered to be a self-consistent sequence of acts and/or operations leading to a desired result. These include physical manipulations of physical quantities. Usually, though not necessarily, these quantities take the form of electrical and/or magnetic signals capable of being stored, transferred, combined, compared, and/or otherwise manipulated. It has proven convenient at times, principally for reasons of common usage, to refer to these signals as bits, values, elements, symbols, characters, terms, numbers and/or the like. It should be understood, however, that all of these and/or similar terms are to be associated with the appropriate physical quantities and are merely convenient labels applied to these quantities.

Unless specifically stated otherwise, as apparent from the following discussions, it is appreciated that throughout the specification discussion utilizing terms such as processing, computing, calculating, determining, and/or the like, refer to the action and/or processes of a computer and/or computing system, and/or similar electronic computing device, that manipulate or transform data represented as physical, such as electronic, quantities within the registers and/or memories of the computer and/or computing system and/or similar electronic and/or computing device into other data similarly represented as physical quantities within the memories, registers and/or other such information storage, transmission and/or display devices of the computing system and/or other information handling system.

Embodiments claimed may include apparatuses for performing the operations herein. This apparatus may be specially constructed for the desired purposes, or it may comprise a general purpose computing device selectively activated and/or reconfigured by a program stored in the device. Such a program may be stored on a storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and/or programmable read only memories (EEPROMs), flash memory, magnetic and/or optical cards, and/or any other type of media suitable for storing electronic instructions, and/or capable of being coupled to a system bus for a computing device and/or other information handling system.

The processes and/or displays presented herein are not inherently related to any particular computing device and/or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments are not described with reference to any particular programming language. It will be appreciated that a variety of programming languages may be used to implement the teachings described herein.

In the following description and/or claims, the terms coupled and/or connected, along with their derivatives, may be used. In one or more embodiments, coupled in ultrasonic testing may describe oil, grease, or water between an ultrasonic probe and the test piece. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect.

Referring now to FIG. 1, a block diagram of a probe system in accordance with one or more embodiments will be discussed. Probe system 100 may comprise probe 110 that may be moved across a surface of a test piece 112, for example along a first axis (X-axis) 116 and/or along a second axis (Y-axis) 118. Probe 110 may comprise a transmitter and/or an array of one or more detector elements. Probe 110 may be coupled to information handling system 114, for example to provide operating power and/or control signals to probe 110, and/or to receive data obtained by probe 110 for example via the array of sensors. Example arrays of probe 110 are shown in and described with respect to FIG. 2, FIG. 3, and/or FIG. 4. An example information handling system 114 is shown in and described with respect to FIG. 7. In one or more embodiments, three or more measurement values per axis to be encoded may be obtained while the probe is not moving. Such three or more values may be utilized to evaluate the direction of the movement along the axis to be encoded. These measurement values may change while the probe is moved. For example, material noise may be different for every probe position, or the remaining wall thickness of a corroded test piece, although the scope of the claimed subject matter is not limited in this respect.

In one or more embodiments, probe system 100 may be utilized to inspect test piece 112, for example to detect flaws and/or defects that may be present in test piece 112. In one such example, test piece 112 may comprise a manufactured part, for example a tube, a T-joint, an aircraft part such as a part of an aircraft engine, aircraft fuselage or wings, and so on. Probe system 100 may be operable to inspect test piece 112 having varying topologies and/or geometries. In one particular embodiment, test piece 112 may comprise an organ, vessel and/or other tissue of a patient such as mammal for example where probe system 100 may be utilized in a health care application. Probe 110 and/or probe system 100 may have a size, shape, and/or other arrangement suitable for the particular application of probe system 100 including but not limited to manufactured parts inspection, health care, and/or surgical applications or the like. However, these are merely example applications in which probe system 100 may be utilized, and the scope of the claimed subject matter is not limited in this respect.

In one or more embodiments, information handling system 114 may comprise a memory having a data file corresponding to test piece 112 to be inspected by probe system 100, although not required. For example, where test piece 112 comprises a manufactured part, such a memory of information handling system 114 may have a computer computer-aided design (CAD) type file or the like being an electronic representation of test piece 112 for design and/or manufacturing purposes. However, a CAD type file is merely one example of a file, but is not required, wherein other graphical and/or image type files may be utilized, and the scope of the claimed subject matter is not limited in this respect. In one or more embodiments, such a CAD type file may comprise a two-dimensional (2-D) representation of test piece 112, and in one or more alternative embodiments, such a CAD type file may comprise a three-dimensional (3-D) representation of test piece 112, although the scope of the claimed subject matter is not limited in this respect.

In one or more embodiments, information handling system 114 may display the CAD type file on a display coupled to information handling system 114 during an inspection of test piece 112 by probe system 112. Concurrently therewith, information handling system 114 may display image data of test piece 112 obtained by probe 110 on the display. This may allow, for example, information handling system 114 to correlate data regarding test piece 112 obtained by probe 110 with the data of test piece 112 contained in the CAD type file. Such a correlation may allow, for example, an operator of probe system 112 to navigate probe 110 along test piece 112 and have a reference to the particular area/and or feature currently being tested with probe 110. For example, when the operator detects a flaw and/or a defect in test piece 112 at a particular location, the operator may be able to determine the location of the flaw with respect to the design data of test piece 112 stored in the CAD type file of test piece 112. Such test data may be mapped onto the data of test piece 112 for future reference and/or study. In one or more embodiments, when the operator detects a flaw and/or defect and/or other noteworthy feature of test piece 112, the operator may store an indication of the location of such a feature, flaw, and/or defect in the CAD type file corresponding to the detected location of the feature, flaw, and/or defect. However, these are merely example applications of probe system 100, and the scope of the claimed subject matter is not limited in this respect.

Figure 2:
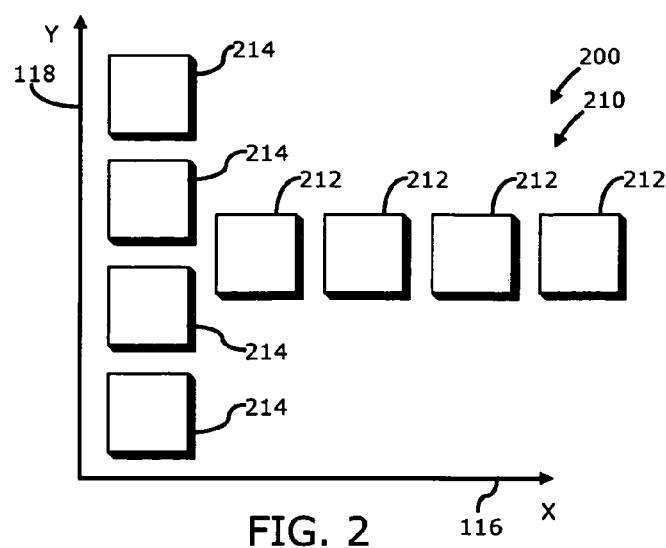
FIG. 2 is a diagram of a sensor array arrangement of a probe in accordance with one or more embodiments.

Referring now to FIG. 2, a diagram of a sensor array arrangement of a probe in accordance with one or more embodiments will be discussed. As shown in FIG. 2, array 200 of sensor elements 212 and/or 214 may be disposed on probe 110 for detecting characteristics of test piece 112. In one embodiment, the sensor elements may comprise ultrasound detector devices, giant magneto impedance (GMI) detector devices, piezoelectric sensors, Hall sensors, Eddy Current sensors, or any other suitable sensor elements or the like. In one or more embodiments, probe 110 may comprise a suitable transmitter for transmitting energy, signals, pulses, and/or impulses that may be detectable by one or more sensors 212 and/or 214 of array 200. Such transmissions may have various timings, durations, shapes, and/or pulse widths. For example, in one or more embodiments, such transmissions may comprise pulse type shapes, and in one or more alternative embodiments, such transmissions may comprise Dirac's delta function type shapes and/or impulses, although the scope of the claimed subject matter is not limited in these respects. Such transmitted signals may also include radio-frequency signals. In one or more embodiments, the operational frequency of probe 110 may be in the range of about 1 MHz to about 25 MHz, for example for testing steel parts or the like, for example to penetrate the material of test piece 112. In one or embodiments, a precision of probe 110 may be less than 1 millimeter, and/or less than 100 micrometers, for example depending on the modality and/or frequency utilized by probe 110. In healthcare applications, probe 110 may comprise a tip of a catheter type device or the like to inspect vessel walls. Shifting of the detected vessel wall pattern in relation to an inner surface of a vessel wall may be determined, and optionally linked to a previously obtained image type file of the vessel, such as a three-dimensional image file, for example as obtained via magnetic resonance imaging (MRI), computed tomography (CT) scanning, or the like, for example to aid in navigating the catheter along the vessel wall and/or in identifying a location of a feature and/or characteristic of interest, or the like, although the scope of the claimed subject matter is not limited in this respect.

In one embodiment, array 200 may comprise a first arrangement 210 of sensor elements 212 and/or 214. In the first arrangement 210, a first row of sensors 212 may be disposed along axis 116, for example to detect movement of probe 110 and/or capture an image and/or other data of test piece 112 along axis 116, and a second row of sensors 214 may be disposed along axis 118, for example to detect movement of probe 110 and/or capture and image and/or other data of test piece 112 along axis 118. Arrangement 210 of array 200 as shown in FIG. 2 may generally comprise a T type shape or the like. In one or more alterative embodiments, variations of arrangement 210 of array 200 may comprise an X type shape or the like, for example where some of sensors 212 may be disposed on one side of the row of sensors 214, and where some of sensors 212 may be disposed on another side of the row of sensors 214. However, these are merely example embodiments of arrangement 210 of array 200, and the scope of the claimed subject matter is not limited in this respect.

Figure 3:
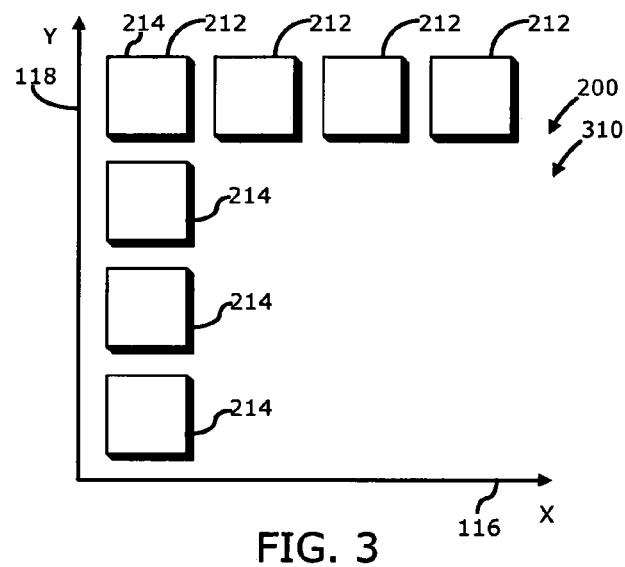
FIG. 3 is a diagram of an alternative sensor array arrangement of a probe in accordance with one or more embodiments.

Referring now to FIG. 3, a diagram of an alternative sensor array arrangement of a probe in accordance with one or more embodiments will be discussed. As shown in FIG. 3, arrangement 310 of array 200 of sensors 212 and/or 214 may comprise an L-type shape or the like. In such an arrangement, and/or variants thereof, at least one or more of sensors in a first row of sensors 212 may also comprise a sensor belonging to a second row of sensors 214 such that the at least one or more such sensors may operate to detect movement of probe 110 and/or an image and/or other data of test piece 112 in both a first direction along axis 116 and/or in a second direction 118, although the scope of the claimed subject matter is not limited in this respect.

Figure 4:
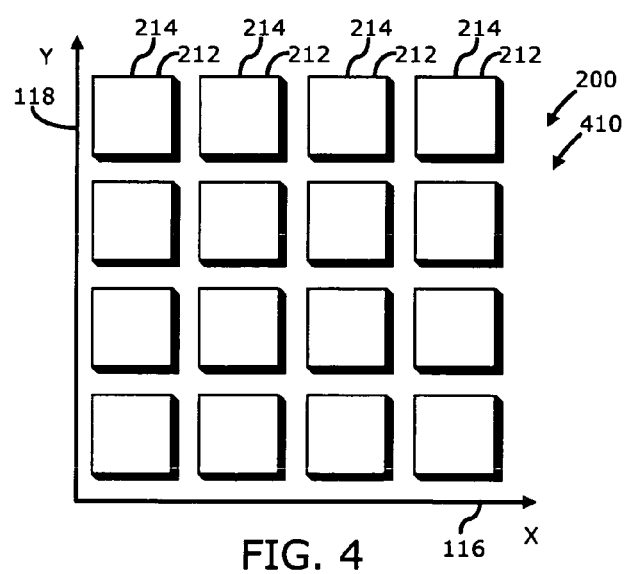
FIG. 4 is a diagram another alternative sensor array arrangement of a probe in accordance with one or more embodiments.

Referring now to FIG. 4, a diagram of another alternative sensor array arrangement of a probe in accordance with one or more embodiments will be discussed. As shown in FIG. 4, arrangement 410 of array 200 may comprise 4 by 4 grid of sensors 212 and/or 214. Although arrangement 410 of FIG. 4 comprises a single 4 by 4 grid of sensors, other arrangements may be utilized as well, for example, one or more sensors in a 1 by 2 grid, in a 1 by 16 grid, a 1 by 128 grid, an 8 by 8 grid, and/or any other arrangement of sensors. The example arrangements 210, 310, and/or 410 of array 200 shown in FIG. 2, FIG. 3, and/or FIG. 4 are merely example arrangements of array 200, and the scope of the claimed subject matter is not limited in this respect.

Figure 5:
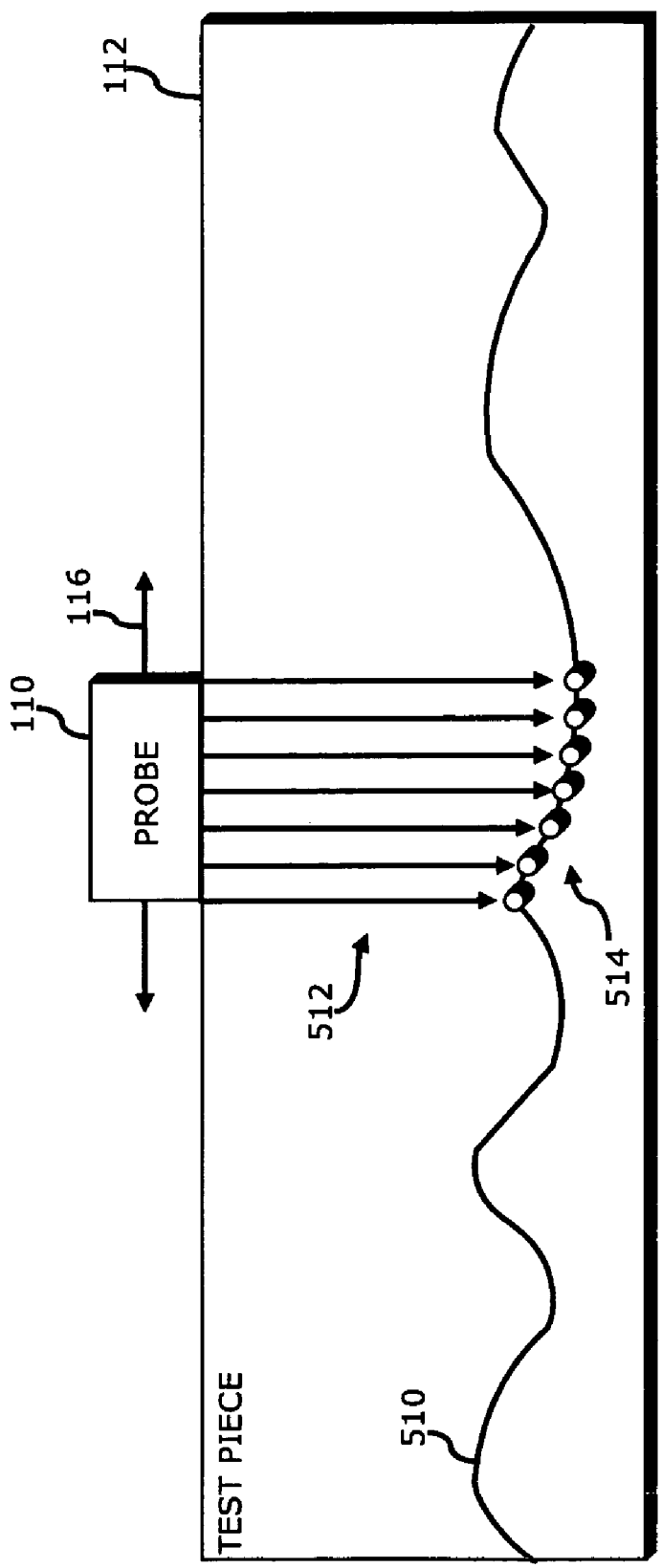
FIG. 5 is a diagram a probe utilized to detect a characteristic, in this example corrosion, of a test piece in accordance with one or more embodiments.

Referring now to FIG. 5, a diagram a probe utilized to detect a characteristic of a test piece in accordance with one or more embodiments will be discussed. As shown in FIG. 5, probe 110 may be moved along axis 116 with respect to test piece 112 as an example. Probe 110 may emit a signal 512 that may at least partially penetrate test piece 112. Signal 512 may be at least partially reflected off of characteristic 510 of test piece, for example as echo signals. In one or more embodiments, while probe 110 is not in movement, three or more values per axis may be obtained and encoded. In one or more embodiments, at least some of signal 512 may be reflected off of characteristic and at least some may pass there through, however probe 110 may detect characteristic 510 for example by detecting at a portion of signal 510 that is reflected off of characteristic 510. In one or more embodiments, an intensity and/or strength of signal 512 may be adjusted, and/or a frequency of signal 512 may be tuned, to select a desired depth of penetration of signal 512 through test piece 112 to sufficiently detect characteristic 510. In one or more embodiments, characteristic 510 may comprise a manufacturing defect and/or flaw, a void, a stress, a fissure, a fracture, a stratum, an inclusion, and/or corrosion for example where test piece 112 is metallic, or the like, although the scope of the claimed subject matter is not limited in this respect. As probe 110 is moved along axis 116 with respect to time, probe 110 may obtain one or more data points 514, and in one particular embodiment, at least three or more data points, corresponding to characteristic 510 detected at periodic time intervals. Movement of probe 110 along axis 116 with respect to test piece 112 may probe 110 to obtain data from which position, velocity, image, and/or other data may be obtained, which may be optionally provide to information handling system 114 where the data may be stored, manipulated, processed, transmitted, and/or displayed, or the like. For example, data of the bulk material internal to test piece 112 may be obtained by probe 110 and an image may be produced there from and displayed on a display of information handling system 114. Such an image may allow the operator to visually inspect test piece 112 and/or visually navigate probe 110 along axis 116 of test piece 112, wherein an image may be utilized for documentation of the test, for example, although the scope of the claimed subject matter is not limited in this respect.

In one or more embodiments, as an example, probe system 100 may be utilized to detect corrosion in test piece 112. Array 200 may comprise an 8 by 8 array of sensors. A virtual probe comprising for example four individual elements may be scanned along a first portion of array 200, for example along 4 by 8 elements. Such a scan may occur electronically in the Y-direction along axis 118, and then may be shifted by one element in the X-direction along axis 116, and then scanning in the Y-direction may be repeated. A multiple dimension scan (C-scan), may be obtained. Such a C-scan may be produced from an echo of signal 512 reflected off of characteristic 510 for example where characteristic 510 comprises corrosion in test piece 110. The coordinates of such a shift may be determined, for example, by comparing multiple C-scans as probe 110 is remaining stationary and/or as probe 110 is moving along test piece 110, which may be in one or more embodiments similar to a method in which an optical mouse detects movement of the mouse such that the first portion of array may be utilized for position data. Another probe element may be utilized to obtain a measurement of the corrosion. In one or more embodiments, the same portion of an array can be used for position data and measurement data such as corrosion. A wide area C-scan may be recorded of the corrosion using the position information obtained by scanning operation of probe 110 together with the corrosion data obtained by the second probe element, although the scope of the claimed subject matter is not limited in this respect. In one or more embodiments, the first probe may comprise a first portion of array 200 and the second probe may comprise a second portion of array 200, or alternatively the first probe may comprise a first array and the second probe may comprise a second array, although the scope of the claimed subject matter is not limited in this respect.

In one or more alternative embodiments, all or nearly all elements of array may be operationally to simultaneously receive echoes of signal 512 and be received by individual sensors 212 and/or 214 of array 200. A C-scan may be produced from such echo signals reflected off of corrosion of characteristic 410, for example as probe remains stationary and/or as probe is moved along axis 116 with respect to test piece 112. Position coordinates may be determined by comparing the C-scans with subsequent scans obtained as probe 112 is moved along axis 116, which may be, for example, in a manner similar to that of an optical mouse. In such an arrangement, the same array may operates as a dual probe to determined position information and/or to obtain data about corrosion characteristic 510, although the scope of the claimed subject matter is not limited in this respect.

In one or more embodiments, a linear scan (B-scan) may be obtained. For such a B-scan, a linear array 200 and/or a linear portion of array 200 may be sufficient. With such a B-scan, probe 110 may move merely along axis 116, for example in the X-direction. As probe 110 is moved along axis 116, multiple B-scans may be obtained, and then subsequently compared to determined movement of probe 110 in the X-directions. The group of B-scans may be utilized to form an image of characteristic 510 of test piece 112, although the scope of the claimed subject matter is not limited in this respect.

In one or more embodiments, for purposes of illustrating a sample calculation, a linear array probe may be utilized. Assuming o elements and p elements of the virtual probe generating k virtual probe positions with k time of flight (TOF) measurements, probe may provide in a start position, for B meaning base position, B(1) . . . B(k) TOF values. While probe 110 is moving, the following readings may be taken and stored, M(1) . . . Mn(k) with M for moving and n number of the consecutive shots. A position of probe 110, where Ppos represents movement in a positive direction along axis 116, may be calculated as:

$$P_{pos} = \min\left\{\sum_{j=1}^{k-1}(B(j+1) - M_n(j))^2\right\}$$

If Ppos has a relative minimum close to zero or equals zero, then probe 110 has been moved one element pitch of probe in the direction of the positive X-axis. Assume m is the number of the readings out of n consecutive readings with Ppos having a minimum as described above: for all j (<=k): B(j)=Mn(j), and the process may repeat.

In parallel with the above calculation of Ppos, Pneg representing movement in a negative direction along axis 116 may be calculated as:

$$P_{neg} = \min\left\{\sum_{j=1}^{k-1}(B(j) - M_n(j+1))^2\right\}$$

If Pneg has a relative minimum close to zero or equal to zero, probe 110 has been moved one element pitch of probe 110 in the direction of the negative X-axis. Assuming m is the number of the reading out of n consecutive readings with Ppos having a minimum as described above, then for all j (<=k): B(j)=Mn(j), and the process may continue. Minima for both Ppos and Pneg are clearly defined and easily determined since only one of the above equations for Ppos and Pneg will have a relative minimum close to zero. The direction of movement of probe 110 may be determined even where, for example, the direction of movement of probe 110 changes before the movement covers one pitch of probe 110. Resolution of the position data may be increased for example by assuming that for a movement of probe a distance of one element pitch of array 200, characteristic 510 may be approximated as a straight line, a correction to the position data may be obtained using an approximation of the curve of the position function, which is a second order parabolic function. Thus, an approximation may be calculated, where delta x may be a correction the position data and delta y may be a given change in B values, as:

$$A(\Delta x) = \sum_{j=1}^{k-1}\{\Delta y_j\}^2$$

Such an approximation may be utilized, for example, to determine a minimum in Ppos and/or Pneg, although the scope of the claimed subject matter is not limited in this respect.

Figure 6:
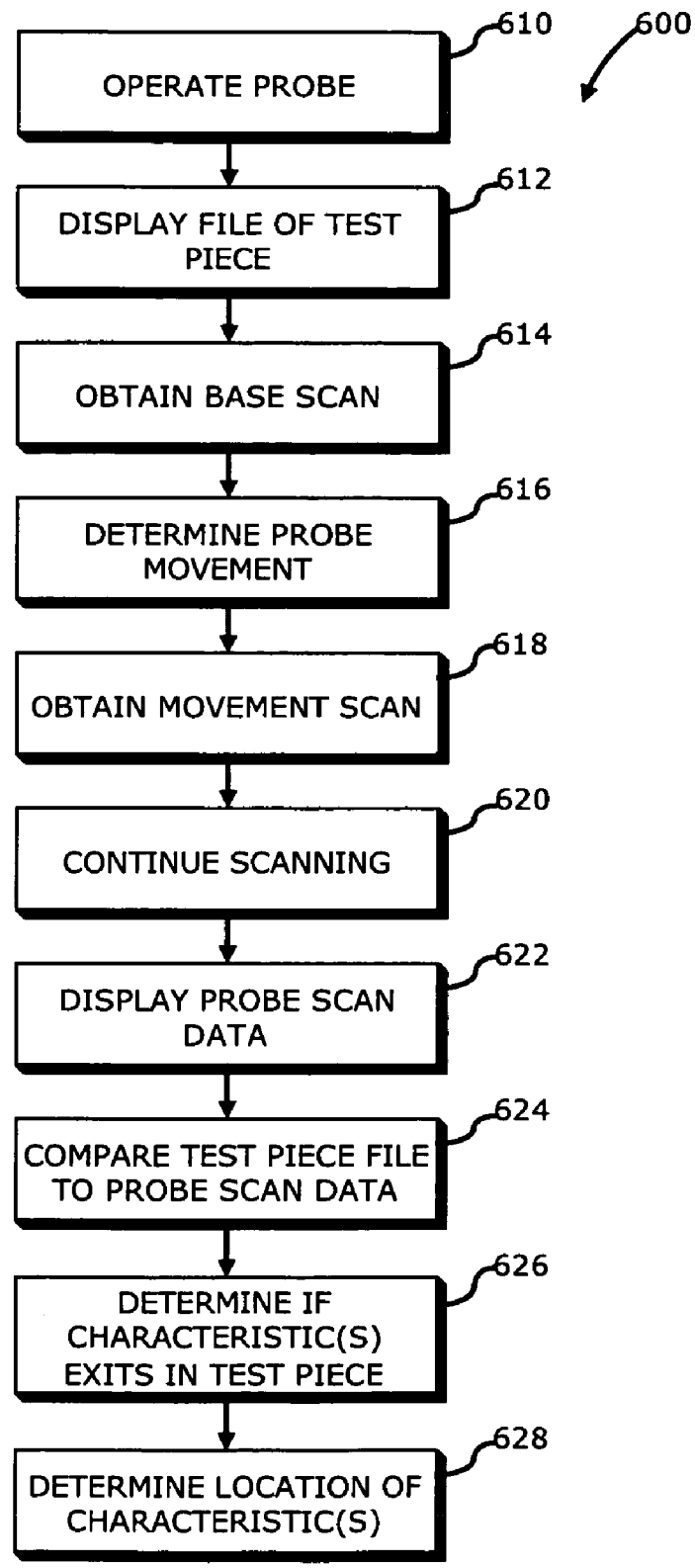
FIG. 6 is a flow diagram of a method for operating a probe in accordance with with one or more embodiments.

Referring now to FIG. 6, a flow diagram of a method for operating a probe in accordance with one or more embodiments will be discussed. Although method 600 as shown in FIG. 6 comprises one particular order of blocks 610 through 628, other orders may be utilized as well, and/or method 600 may comprise more and/or fewer blocks than shown in FIG. 6, and the scope of the claimed subject matter is not limited in this respect. Probe 110 of probe system 100 may be operated at block 610, for example to obtain data of test piece 122. Information handling system 114 may optionally display a file of test piece 112 on a display, for example a CAD type file of test piece 112, for example to provide a reference for an operator of probe system 100. A base scan of test piece 112 may be obtained at block 614, for example while probe 110 is remaining stationary and/or nearly stationary, and/or at an initial phase of movement of probe 110. Movement of probe 110 may be determined at block 616, where for example position, direction, and/or velocity information regarding movement of probe 110 with respect to test piece 112 may be determined. After a predetermined amount of movement of probe 110 and/or a predetermined amount of time for which probe 110 has been moving, a subsequent scan with probe 110 may be obtained at block 618. Scanning with probe 110 may continue at block 620, for example at a new position of probe 110 and/or as probe 110 continues to move with respect to test piece 110.

In one or more embodiments, probe scan data obtained with probe 110 optionally may be displayed on a display of information handling system 114, which may occur, for example, during operation of probe system 100 such that an image of what is being scanned by probe 110 may be displayed at block 622 on the display and viewable by the operator, for example to assist the operator with navigation of probe 110 along test piece 112. The file of test piece 112 optionally may be compared at block 624 with probe scan data obtained with probe 100, for example an electronic version of test piece as rendered from the CAD type file may be superimposed with an image of test piece 112 obtained with probe 110, for example so that a characteristic of test piece 112 may be correlated with one or more coordinates of the position of probe 110 and of test piece 112 from the CAD type file. A determination may be made at block 626 whether a characteristic of interest, such as characteristic 510, exists in test piece 112, where the characteristic of interest may comprise, for example, comprise a manufacturing defect and/or flaw, a void, a stress, a fissure, a fracture, a stratum, an inclusion, and/or corrosion for example where test piece 112 is metallic, or the like. Such a determination may be made, for example, via visual identification of such a characteristic by the operator of probe system 100 based at least in part on an image of test piece 112 obtained with probe 110, or alternatively such a determination may be made based at least in part on a software programming executable by information handling system 114.

Figure 7:
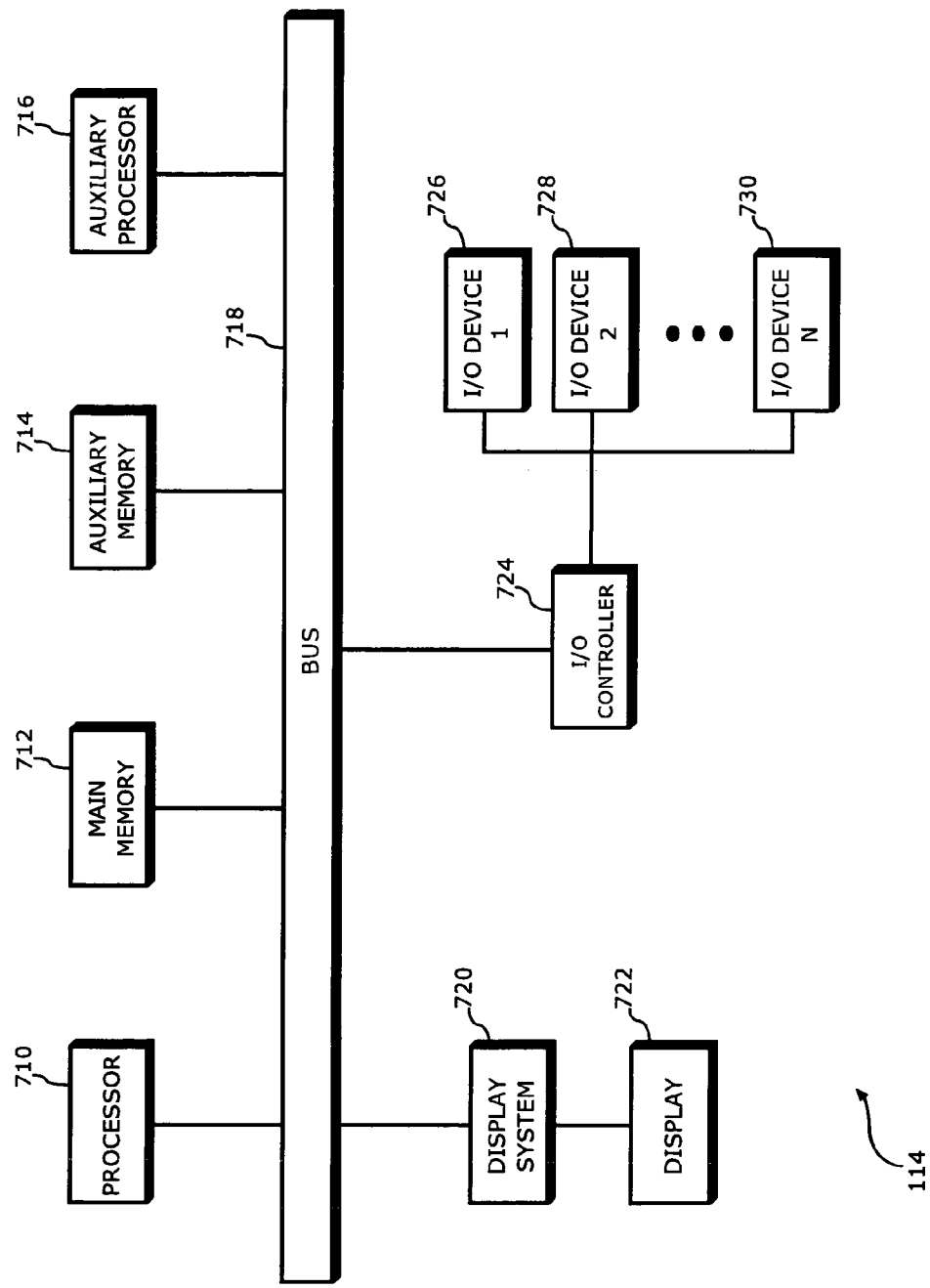
FIG. 7 is a block diagram of an information handling system capable of operating with a probe in accordance with one or more embodiments.

Referring now to FIG. 7, a block diagram of an information handling system capable of operating with a probe in accordance with one or more embodiments will be discussed. Information handling system 114, as shown in FIG. 1 and/or in FIG. 7, may be utilized to tangibly embody a computer program and/or graphical user interface by providing hardware components on which the computer program and/or graphical user interface 110 may be executed, for example to execute method 600 of FIG. 6. Such a computer program and/or machine readable instructions may be tangibly stored on a computer and/or machine readable medium such as a compact disk (CD), digital versatile disk (DVD), flash memory device, hard disk drive (HDD), and so on. As shown in FIG. 7, information handling system 114 may be controlled by processor 710. Processor 710 may comprise a central processing unit such as a microprocessor or microcontroller for executing programs, performing data manipulations and controlling the tasks of information handling system 114. Communication with processor 710 may be implemented via bus 718 for transferring information among the components of information handling system 114. Bus 718 may include a data channel for facilitating information transfer between storage and other peripheral components of information handling system 718. Bus 718 further may provide a set of signals utilized for communication with processor 710, including, for example, a data bus, and address bus, and/or a control bus. Bus 718 may comprise any bus architecture according to promulgated standards, for example industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and so on, although the scope of the claimed subject matter is not limited in this respect.

Other components of information handling system may include, for example, main memory 712, and/or auxiliary memory 714. Information handling system 114 may further comprise auxiliary processing processor 716, which may be another processor, a digital signal processor, and so on. Main memory 712 may provide storage of instructions and data for programs to be executed by processor 710. Main memory 712 may be, for example, semiconductor-based memory such as dynamic random access memory (DRAM) and/or static random access memory (SRAM), and/or the like. Other semi-conductor-based memory types may include, for example, synchronous dynamic random access memory (SDRAM), Rambus dynamic random access memory (RDRAM), ferroelectric random access memory (FRAM), and so on. Auxiliary memory 712 may be utilized to store instructions and/or data that to be loaded into main memory 712 before execution. Auxiliary memory 714 may include semiconductor based memory such as read-only memory (ROM), programmable read-only memory (PROM), erasable programmable read-only memory (EPROM), electrically erasable read-only memory (EEPROM), and/or flash memory, and/or any block oriented memory similar to EEPROM. Auxiliary memory 714 may also include any type of non-semiconductor-based memories, including but not limited to magnetic tape, drum, floppy disk, hard disk, optical, laser disk, compact disc read-only memory (CD-ROM), write once compact disc (CD-R), rewritable compact disc (CD-RW), digital versatile disc read-only memory (DVD-ROM), write once DVD (DVD-R), rewritable digital versatile disc (DVD-RAM), and so on. Other varieties of memory devices are contemplated as well. Information handling system 114 optionally include auxiliary processor 716 which may be an auxiliary processor to manage input/output, an auxiliary processor to perform floating point mathematical operations, a digital signal processor and/or any special-purpose microprocessor having an architecture suitable for fast execution of signal processing algorithms, a back-end processor and/or any slave type processor subordinate to processor 710, an additional microprocessor and/or controller for dual and/or multiple processor systems, and/or a coprocessor and/or additional processor. Such auxiliary processors may be discrete processors and/or may be arranged in the same package as processor 410, for example in a multicore and/or multithreaded processor, however the scope of the claimed subject matter is not limited in these respects.

Information handling system 114 further may include display system 720 for connecting to display 722, and further may include input/output (I/O) controller 724 to connect to one or more I/O devices including, for example, I/O device 726, I/O device 728, up to an Nth I/O device, I/O device 730. Display system 720 may comprise a video display adapter having components for driving display 722, including, for example, video memory, a buffer, and/or a graphics engine. Such video memory may be, for example, video random access memory (VRAM, synchronous graphics random access memory (SGRAM), windows random access memory (WRAM), and/or the like. Display 722 may comprise a cathode ray-tube (CRT) type display such as a monitor and/or television, and/or may comprise an alternative type of display technology such as a projection type CRT type display, a liquid-crystal display (LCD) projector type display, an LCD type display, a light-emitting diode (LED) type display, a gas and/or plasma type display, an electroluminescent type display, a vacuum fluorescent type display, a cathodoluminescent and/or field emission type display, a plasma addressed liquid crystal (PALC) type display, a high gain emissive display (HGED) type display, and so forth. Input/output controller 724 may comprise one or more controllers and/or adapters to prove interface functions between one or more of I/O device 726, I/O device 728, and/or I/O device 730. For example, input/output controller 724 may comprise a serial port, parallel port, universal serial bus (USB) port, and-IEEE 1394 serial bus port, infrared port, network adapter, printer adapter, radio-frequency (RF) communications adapter, universal asynchronous receiver-transmitter (UART) port, and/or the like, to interface between corresponding I/O devices such as a keyboard, mouse, trackball, touchpad, joystick, track stick, infrared transducers, printer, modem, RF modem, bar code reader, charge-coupled device (CCD) reader, scanner, compact disc (CD), compact disc read-only memory (CD-ROM), digital versatile disc (DVD), video capture device, TV tuner card, touch screen, stylus, electroacoustic transducer, microphone, speaker, audio amplifier, and/or the like. Input/output controller 724 and/or I/O device 726, I/O device 728, and/or I/O device 730 may provide and/or receive analog and/or digital signals to communicate between information handling system and external devices, networks, and/or information sources. Input/output controller 724 and/or I/O device 726, I/O device 728, and/or I/O device 730 may implement industry promulgated architecture standards, including, for example, Ethernet IEEE 802 type standards, such as IEEE 802.3 for broadband and/or baseband networks, IEEE 802.3z for Gigabit Ethernet, IEEE 802.4 for token passing bus networks, IEEE 802.5 for token ring networks, IEEE 802.6 for metropolitan area networks and/or the like, Fibre Channel, digital subscriber line (DSL), asymmetric digital subscriber line (ASDL), flame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on. Information handling system 114 of FIG. 7 is merely one example of an information handling system and/or computing platform, and the scope of the claimed subject matter is not limited in this respect.

Although the claimed subject matter has been described with a certain degree of particularity, it should be recognized that elements thereof may be altered by persons skilled in the art without departing from the spirit and/or scope of the claimed subject matter. It is believed that the sensor array for navigation on surfaces and/or many of its attendant advantages will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. An apparatus, comprising:
a transmitter configured to transmit a signal capable of at least partially penetrating a test piece that is coupled to the transmitter;
an array of at least one or more sensors capable of detecting at least a portion of the signal reflected back from the test piece, said array comprising a grid of at least three sensors arranged in a first number of rows of sensors and a second number of columns of sensors; and
an information handling system configured to receive data from the array and to determine at least one of movement data of the array or data of a characteristic of the test piece, or a combination thereof.

2. An apparatus as claimed in claim 1, said array being capable of measuring three or more values per axis to be encoded.

3. An apparatus as claimed in claim 1, wherein the data of the characteristic comprises image data of the test piece.

4. An apparatus as claimed in claim 1, wherein the characteristic of the test piece comprise at least one or more of a manufacturing defect, a flaw, a void, a stress, a fissure, a fracture, a stratum, an inclusion, or corrosion, or a combination thereof.

5. An apparatus as claimed in claim 1, said array comprising a linear array of the at least three or more sensors.

6. An apparatus as claimed in claim 1, said array comprising a first linear array of the at least three or more sensors and a second linear array of the at least three or more sensors, the first linear array being orthogonally disposed with respect to the second linear array.

7. An apparatus as claimed in claim 1, the at least one or more sensors comprising at least one or more of an ultrasound sensor, a magneto impedance sensor, a Hall sensor, Eddy Current sensor, a piezoelectric sensor, or a radio-frequency sensor, or a combination thereof.

8. An apparatus as claimed in claim 1, at least one of said transmitter or said array being disposed on a catheter type device.

9. A method, comprising:
transmitting a signal capable of at least partially penetrating a test piece;
detecting at least a portion of the signal reflected from the test piece;
determining at least one of movement data or data of a characteristic of the test piece, or a combination thereof, in response to said detecting;
generating image data of the test piece based at least in part on said determining; and
displaying the image data on a display and concurrently displaying on the display a rendition of the test piece generated from a data file of the test piece in accordance with a probe position.

10. A method as claimed in claim 9, further comprising generating image data of the test piece based at least in part on said determining.

11. A method as claimed in claim 9, further comprising generating image data of the characteristic of test piece based at least in part on said determining.

12. A method as claimed in claim 9, further comprising generating image data of the test piece based at least in part on said determining, and displaying the image data on a display.

13. A method as claimed in claim 9, further comprising generating image data of the test piece based at least in part on said determining, displaying the image data on a display, and updating the image data based at least in part on the movement data.

14. A method as claimed in claim 9, further comprising generating image data of the test piece based at lest in part on said determining, displaying the image data on a display, and concurrently displaying on the display a rendition of the test piece generated from a computer aided design type file of the test piece.

15. A method as claimed in claim 9, further comprising correlating at least one of the movement data or the data of a characteristic of the test piece, or a combination thereof, with a data file of the test piece.

16. A method as claimed in claim 9, further comprising correlating at least one of the movement data or the data of a characteristic of the test piece, or a combination thereof, with a computer aided design type file of the test piece.

17. A method as claimed in claim 9, further comprising identifying the characteristic based at least in part on the data of the characteristic or the movement data, or a combination thereof, and correlating the characteristic with a coordinate of the test piece in a data file of the test piece.

18. A method as claimed in claim 9, further comprising identifying the characteristic based at least in part on the data of the characteristic or the movement data, or a combination thereof, and correlating the characteristic with a coordinate of the test piece in computer aided design type file of the test piece.

19. A probe system, comprising:
an information handling system; and
a probe capable of coupling with said information handling system, said probe comprising:
a transmitter to transmit a signal capable of at least partially penetrating a test piece; and
an array of at least one or more sensors capable of detecting at least a portion of the signal reflected back from the test piece, said array comprising a grid of the at least one or more sensors arranged in a first number of rows of sensors and a second number of columns of sensors;
wherein, in response to said array detecting at least a portion of the reflected signal, said information handling system is capable of determining at least one of movement data of the array or data of a characteristic of the test piece, or a combination thereof.

20. A probe system as claimed in claim 19, said array being capable of measuring three or more values per axis to be encoded.

21. A probe system as claimed in claim 19, wherein the data of the characteristic comprises image data of the test piece.

22. A probe system as claimed in claim 19, wherein the characteristic of the test piece comprise at least one or more of a manufacturing defect, a flaw, a void, a stress, a fissure, a fracture, a stratum, an inclusion, or corrosion, or a combination thereof.

23. A probe system as claimed in claim 19, said array comprising a linear array of the at least three or more sensors.

24. A probe system as claimed in claim 19, said array comprising a first linear array of the at least three or more sensors and a second linear array of the at least three or more sensors, the first linear array being orthogonally disposed with respect to the second linear array.

25. A probe system as claimed in claim 19, the at least one or more sensors comprising at least one or more of an ultrasound sensor, a magneto impedance sensor, a Hall sensor, Eddy Current sensor, a piezoelectric sensor, or a radio-frequency sensor, or a combination thereof.

26. A probe system as claimed in claim 19, at least one of said transmitter or said array, or a combination thereof, being disposed on a catheter type device.

* * * * *

UNITED STATES PATENT AND TRADEMARK OFFICE
CERTIFICATE OF CORRECTION

| | | |
|---|---|---|
| PATENT NO. | : 7,324,910 B2 | Page 1 of 1 |
| APPLICATION NO. | : 11/317098 | |
| DATED | : January 29, 2008 | |
| INVENTOR(S) | : Struempler et al. | |

It is certified that error appears in the above-identified patent and that said Letters Patent is hereby corrected as shown below:

In Fig. 6, Sheet 4 of 5, for Tag "626", Line 3, delete "EXITS" and insert -- EXISTS --, therefor.

In Column 11, Line 46, delete "flame" and insert -- frame --, therefor.

In Column 13, Line 7, in Claim 14, delete "at lest" and insert -- at least --, therefor.

Signed and Sealed this

Twenty-sixth Day of May, 2009

JOHN DOLL
*Acting Director of the United States Patent and Trademark Office*